United States Patent
Yamane

(10) Patent No.: US 11,402,520 B2
(45) Date of Patent: Aug. 2, 2022

(54) PARTICLE DETECTOR, IMAGE GENERATION DEVICE, AND IMAGE GENERATION METHOD

(71) Applicant: KIOXIA CORPORATION, Tokyo (JP)

(72) Inventor: Takeshi Yamane, Tsukuba Ibaraki (JP)

(73) Assignee: Kioxia Corporation, Tokyo (JP)

( * ) Notice: Subject to any disclaimer, the term of this patent is extended or adjusted under 35 U.S.C. 154(b) by 138 days.

(21) Appl. No.: 16/505,798

(22) Filed: Jul. 9, 2019

(65) Prior Publication Data

US 2020/0033488 A1 Jan. 30, 2020

(30) Foreign Application Priority Data

Jul. 25, 2018 (JP) .............................. JP2018-139490

(51) Int. Cl.
  *G01T 1/16* (2006.01)
  *G01T 1/24* (2006.01)
  (Continued)

(52) U.S. Cl.
  CPC ............. *G01T 1/242* (2013.01); *G01N 21/17* (2013.01); *G01T 1/241* (2013.01); *H01L 31/101* (2013.01);
  (Continued)

(58) Field of Classification Search
  CPC ....... G01T 1/242; G01T 1/241; G01T 1/1606; G01N 21/17; H01L 31/101; H01L 31/115;
  (Continued)

(56) References Cited

U.S. PATENT DOCUMENTS 4,873,482 A * 10/1989 Gray ..................... G01T 1/1606
                                                324/71.4
6,812,464 B1    11/2004 Sobolewski et al.
                  (Continued)

FOREIGN PATENT DOCUMENTS

JP          2011-164068 A      8/2011
JP              5027965 B2     9/2012
                  (Continued)

OTHER PUBLICATIONS

Fukuda et al., "Superconducting Single Photon Detectors," The Journal of Institute of Electronics, Information and Communication Engineers (Aug. 2007), 90:674-679.
(Continued)

*Primary Examiner* — David P Porta
*Assistant Examiner* — Shun Lee
(74) *Attorney, Agent, or Firm* — Finnegan, Henderson, Farabow, Garrett & Dunner L.L.P.

(57) ABSTRACT

According to one embodiment, a particle detector is disclosed. The particle detector includes a substrate, and detection regions provided on the substrate and insulated from the substrate. Each of the detection regions includes superconducting strips having a longitudinal direction and configured for detecting a particle, and the superconducting strips are arranged in arrangement directions differing between the detection regions. The numbers of particles detected by the respective detection regions are used to generate accumulated detection number profiles of particles in the arrangement directions of the superconducting strips of the respective detection regions, and each of the accumulated detection number profiles includes a profile obtained by accumulating the numbers of particles detected by the respective superconducting strips along the longitudinal direction.

19 Claims, 11 Drawing Sheets

(51) Int. Cl.
  *G01N 21/17* (2006.01)
  *H01L 31/101* (2006.01)
  *H01L 39/02* (2006.01)
  *A61B 6/03* (2006.01)
  *A61B 6/00* (2006.01)

(52) U.S. Cl.
  CPC .............. *H01L 39/02* (2013.01); *A61B 6/032* (2013.01); *A61B 6/52* (2013.01)

(58) Field of Classification Search
  CPC ......... H01L 39/02; H01L 39/10; A61B 6/032; A61B 6/52
  See application file for complete search history.

(56) References Cited

U.S. PATENT DOCUMENTS

2016/0260596 A1* 9/2016 McDermott, III .... H01J 49/025
2017/0150936 A1 6/2017 Yoda
2017/0248532 A1* 8/2017 Kadambi ............. G01N 23/046
2018/0188107 A1 7/2018 Zen et al.

FOREIGN PATENT DOCUMENTS

| JP | 5846574 B2 | 1/2016 |
| JP | 2017-9372 A | 1/2017 |
| JP | 2017-104531 A | 6/2017 |

OTHER PUBLICATIONS

Inderbitzin et al., "Soft X-Ray Single-Photon Detection With Superconducting Tantalum Nitride and Niobium Nanowires," IEEE Transactions on Applied Superconductivity (Dec. 12, 2012), 23:1-5.
Miura et al., "Image Restoration and Reconstruction," Kogaku: Japanese Journal of Optics (2002), 31:636-642.

* cited by examiner

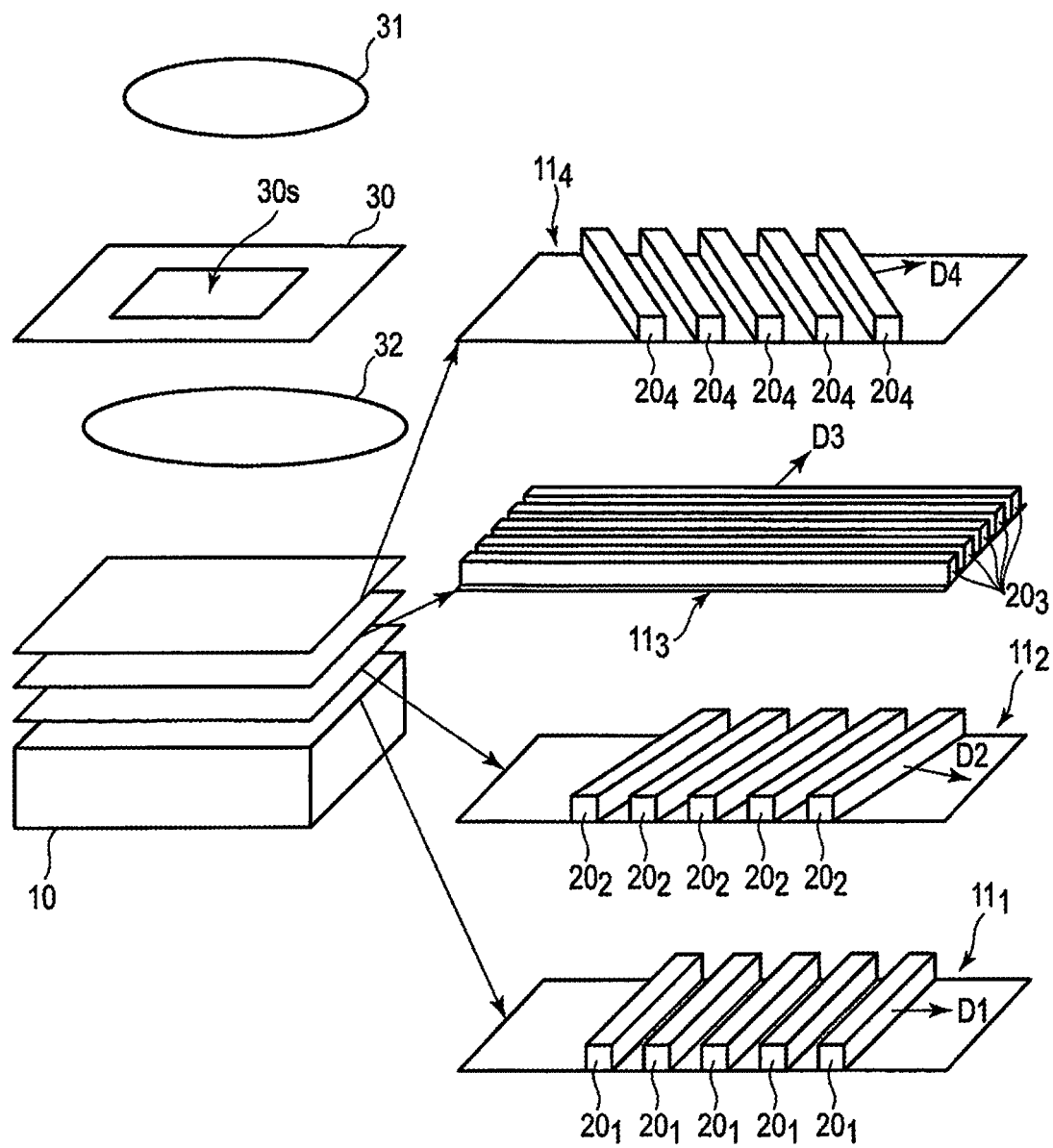
F I G. 1

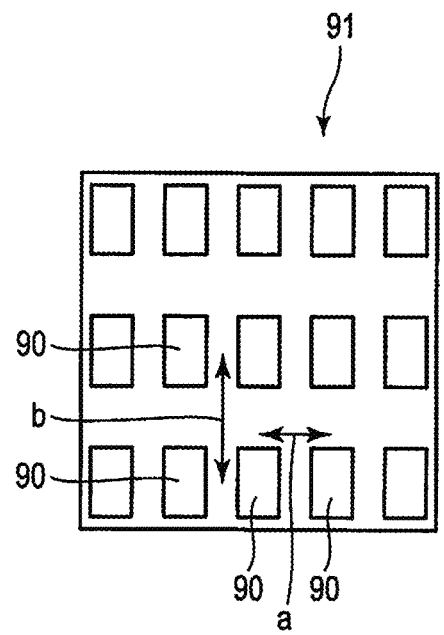
F I G. 12A
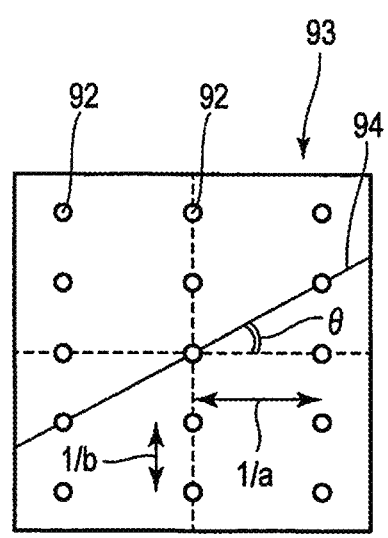
F I G. 12B

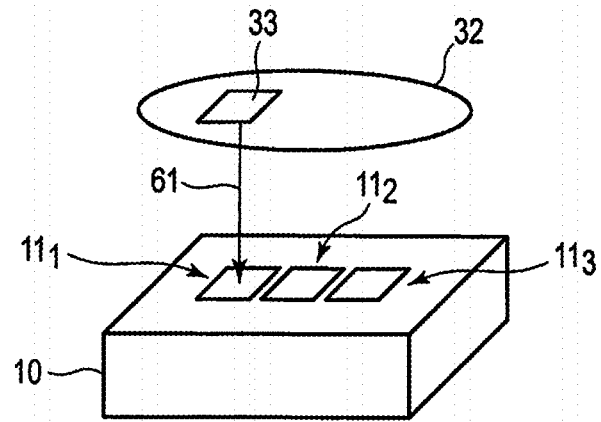
F I G. 14A
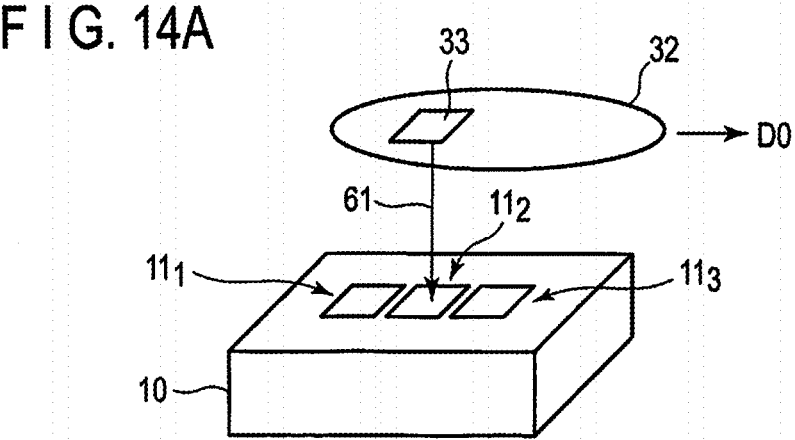
F I G. 14B
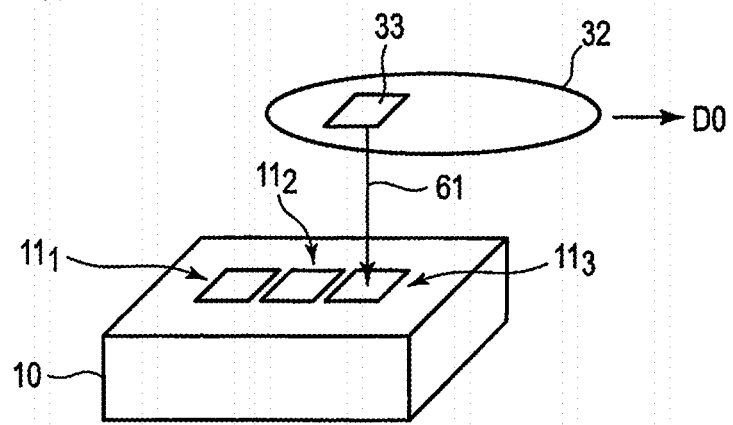
F I G. 14C

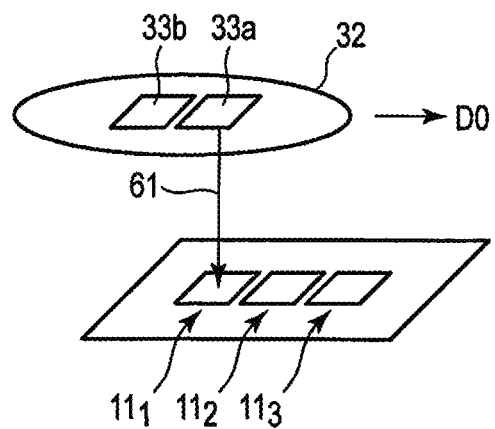
F I G. 15A
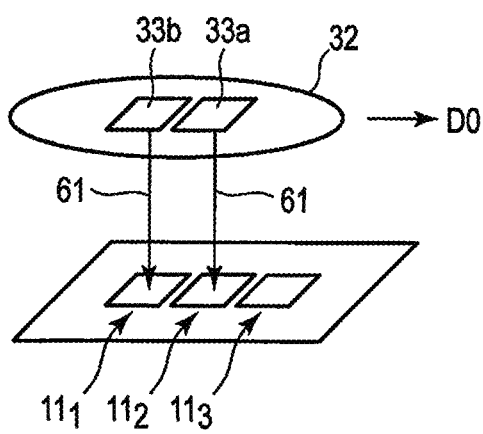
F I G. 15B
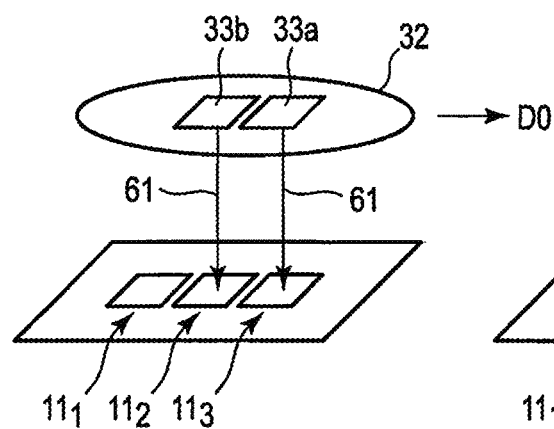
F I G. 15C
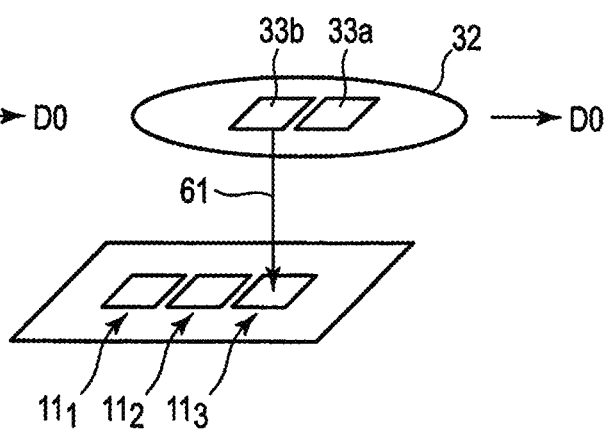
F I G. 15D

PARTICLE DETECTOR, IMAGE GENERATION DEVICE, AND IMAGE GENERATION METHOD

CROSS-REFERENCE TO RELATED APPLICATIONS

This application is based upon and claims the benefit of priority from Japanese Patent Application No. 2018-139490, filed Jul. 25, 2018, the entire contents of which are incorporated herein by reference.

FIELD

Embodiments described herein relate generally to a particle detector, an image generation device, and an image generation method.

BACKGROUND

An X-ray photon detection device employing a narrow strip made of a superconducting material (superconducting strip) has been known. When detecting an X-ray photon, a bias current is supplied to the superconducting strip in a superconducting state. When the X-ray photon collides with the superconducting strip in this state, a temporal transition to a non-superconducting state arises in the vicinity of a region with which the X-ray photon collides, and thus a pulsed electrical signal is generated. The pulsed electrical signal is detected to count the number of X-ray photons.

BRIEF DESCRIPTION OF THE DRAWINGS

FIG. 1 is a perspective view showing a schematic structure of a particle detector according to a first embodiment.

FIG. 12A and FIG. 12B are diagrams showing a periodic pattern of a sample used in a particle detector according to a third embodiment and a Fourier transform image of the periodic pattern.

FIG. 14A, FIG. 14B, and FIG. 14C are diagrams for explaining an image generation method employing the particle detector according to the fourth embodiment.

FIG. 15A, FIG. 15B, FIG. 15C, and FIG. 15D are diagrams for explaining another image generation method employing the particle detector according to the fourth embodiment.

DETAILED DESCRIPTION

Figure 2A:
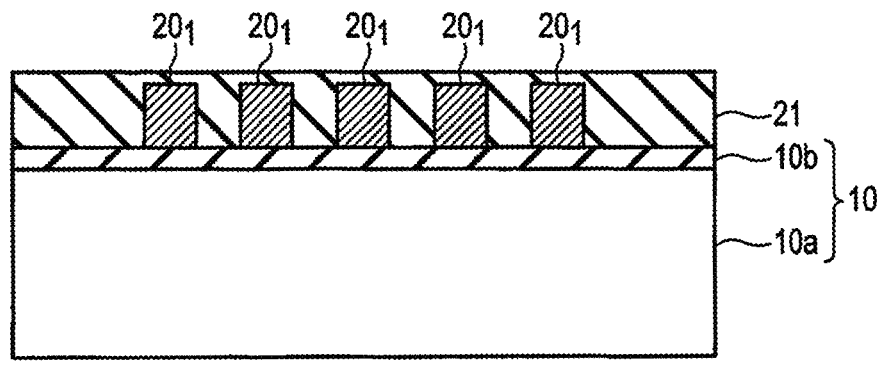
FIG. 2A, FIG. 2B, and FIG. 2C are sectional views for explaining a detection region of the particle detector.

In general, according to one embodiment, a particle detector is disclosed. The particle detector comprises a substrate, and detection regions provided on the substrate and insulated from the substrate. Each of the detection regions comprises superconducting strips having a longitudinal direction and configured for detecting a particle, and the superconducting strips are arranged in arrangement directions differing between the detection regions. The numbers of particles detected by the respective detection regions are used to generate accumulated detection number profiles of particles in the arrangement directions of the superconducting strips of the respective detection regions, and each of the accumulated detection number profiles includes a profile obtained by accumulating the numbers of particles detected by the respective superconducting strips along the longitudinal direction.

Embodiments will be described hereinafter with reference to the accompanying drawings. The drawings are schematic or conceptual drawings, and dimensions and ratios are not necessarily the same as those in reality. Further, in the drawings, the same reference symbols (including those having different subscripts) denote the same or corresponding parts, and overlapping explanations thereof will be made as necessary. In addition, as used in the description and the appended claims, what is expressed by a singular form shall include the meaning of "more than one".

First Embodiment

FIG. 1 is a perspective view showing a schematic structure of a particle detector according to a first embodiment. In the present embodiment, description is given for a case where the particle detector detects an X-ray photon, which is an example of a particle.

The particle detector of the present embodiment includes a substrate 10, a first detection region $11_1$ provided on the substrate 10, a second detection region $11_2$ provided on the first detection region $11_1$, a third detection region $11_3$ provided on the second detection region $11_2$, and a fourth detection region $11_4$ provided on the third detection region $11_3$. Although the number of detection regions (the number of stacked layers) is four in the present embodiment, the number may be two, three, five or more.

As shown in the sectional view of FIG. 2A, the substrate 10 includes a semiconductor substrate $10a$ and an insulating layer $10b$ provided thereon. The semiconductor substrate $10a$ is, for example, a silicon substrate, and the insulating layer $10b$ is, for example, a silicon dioxide layer.

The first detection region $11_1$ to the fourth detection region $11_4$ are provided in order on the insulating layer $10b$. As a result, the first detection region $11_1$ to the fourth detection region $11_4$ are stacked on the substrate 10 in the state of being insulated from the substrate 10.

The first detection region $11_1$ includes first superconducting strips $20_1$. An arrangement direction of the first superconducting strips $20_1$ is a first direction D1. A longitudinal direction of the first superconducting strips $20_1$ is a direction perpendicular to the first direction D1. The first superconducting strips $20_1$ are, for example, arranged periodically.

The width and the thickness of the first superconducting strips $20_1$ are less than or equal to 200 nm. This is because the sectional areas of the first superconducting strips $20_1$ are made smaller to the extent that superconducting regions are divided. A well-known material can be selected as appropriate as the materials of the first superconducting strips $20_1$. As in the case of a material including tantalum, the greater the absorptance of X-rays is, the greater the detection efficiency of X-ray photons is.

Although the number of first superconducting strips $20_1$ is five in the present embodiment, the number may be four, three, two, six or more.

As shown in the sectional view of FIG. 2A, the first detection region $11_1$ further includes a first insulating layer 21 covering the first superconducting strips $20_1$. The material of the first insulating layer 21 is, for example, silicon dioxide. The surface of the first insulating layer 21 is planarized by polishing.

The second detection region $11_2$ includes second superconducting strips $20_2$ of which arrangement direction is a second direction D2 different from the first direction D1. A longitudinal direction of the second superconducting strips $20_2$ is a direction perpendicular to the second direction D2. The second superconducting strips $20_2$ are, for example, arranged periodically.

The second superconducting strips $20_2$ are provided on the first insulating layer 21 shown in FIG. 2A. The second detection region $11_2$ further includes a second insulating layer corresponding to the first insulating layer 21 shown in FIG. 2A. The dimensions, the number, and the superconducting materials of the second superconducting strips $20_2$ are the same as those of the first superconducting strips $20_1$.

The third detection region $11_3$ includes third superconducting strips $20_3$ of which arrangement direction is a third direction D3 different from the first direction D1 and the second direction D2. A longitudinal direction of the third superconducting strips $20_3$ is a direction perpendicular to the third direction D3. The third superconducting strips $20_3$ are, for example, arranged periodically.

The third superconducting strips $20_3$ are provided on the above-described second insulating layer. The third detection region $11_3$ further includes a third insulating layer corresponding to the first insulating layer 21 shown in FIG. 2A.

The dimensions, the number, and the superconducting materials of the third superconducting strips $20_3$ are the same as those of the first superconducting strips $20_1$.

The fourth detection region $11_4$ includes fourth superconducting strips $20_4$ of which arrangement direction is a fourth direction D4 different from the first direction D1, the second direction D2, and the third direction D3. A longitudinal direction of the fourth superconducting strips $20_4$ is a direction perpendicular to the fourth direction D4. The fourth superconducting strips $20_4$ are, for example, arranged periodically.

Figure 2B:
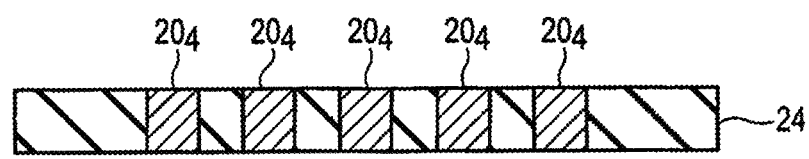
Figure 2C:
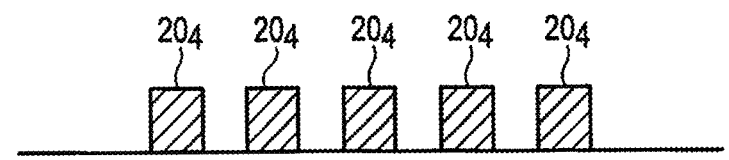

The fourth superconducting strips $20_4$ are provided on the above-described third insulating layer. For example, as shown in the sectional view of FIG. 2B, the fourth detection region $11_4$ further includes a fourth insulating layer 24 covering the side surfaces of the fourth superconducting strips $20_4$. The fourth insulating layer 24 does not cover the top surfaces of the fourth superconducting strips $20_4$. An X-ray photon is incident on the top surfaces of the fourth superconducting strips $20_4$. The top surfaces may be covered by the fourth insulating layer 24 or other layers (for example, a protective layer), as long as an X-ray photon can be incident on the top surfaces. Note that, the fourth insulating layer 24 may not be provided in the fourth detection region $11_4$, for example, as shown in the sectional view of FIG. 2C.

The number and the superconducting materials of the fourth superconducting strips $20_4$ are the same as those of the first superconducting strips $20_1$.

As described above, an X-ray photon is incident on the fourth detection region $11_4$ (detection region in the highest layer). The incident X-ray photon is absorbed by any one of the fourth superconducting strips $20_4$ of the fourth detection region $11_4$, any one of the third superconducting strips $20_3$ of the third detection region $11_3$, any one of the second superconducting strips $20_2$ of the second detection region $11_2$ or any one of the first superconducting strips $20_1$ in the first detection region $11_1$ (detection region in the lowest layer), or the incident X-ray photon passes through the fourth detection region $11_4$ to the first detection region $11_1$, and reaches the substrate 10.

By determining the number of stacked layers so that a certain number of X-ray photons are absorbed by the detection region of the lowest layer, the probability of detection of X-ray photons increases. Thus, a detection failure, i.e., a failure to detect X-ray photons, can be prevented from occurring. In addition, also in cases where X-ray photons which are incident at the same time are detected by any one of the detection region in the highest layer to the detection region in the lowest layer, all the X-ray photons can be detected.

The particle detector of the present embodiment may include a slit portion 30 which is disposed above the fourth detection region $11_4$ and which limits a region of X-rays to be detected. Reference symbol 30s represents an opening portion of the slit portion 30 (slit opening portion). The shape of the slit-portion opening 30s is determined so that the region of X-rays pass through the slit-portion opening 30s is included in a region where superconducting strips are arranged in all of the fourth detection region $11_4$ to the first detection region $11_1$. When the slit portion 30 is not included in a part of the particle detector, the slit portion 30 is prepared when detecting an X-ray photon.

The particle detector of the present embodiment may include an X-ray generator 31 which is disposed above the slit portion 30 and which generates X-rays. When the X-ray generator 31 is not included in a part of the particle detector, the X-ray generator 31 is prepared when detecting an X-ray photon.

In the following description, when it is unnecessary to distinguish the first to fourth superconducting strips $20_1$ to $20_4$ in particular, they will be referred to as superconducting strips $20_i$. Similarly, when it is unnecessary to distinguish the first to fourth detection regions $11_1$ to $11_4$ in particular, they will be referred to as detection regions $11_i$.

Figure 3:
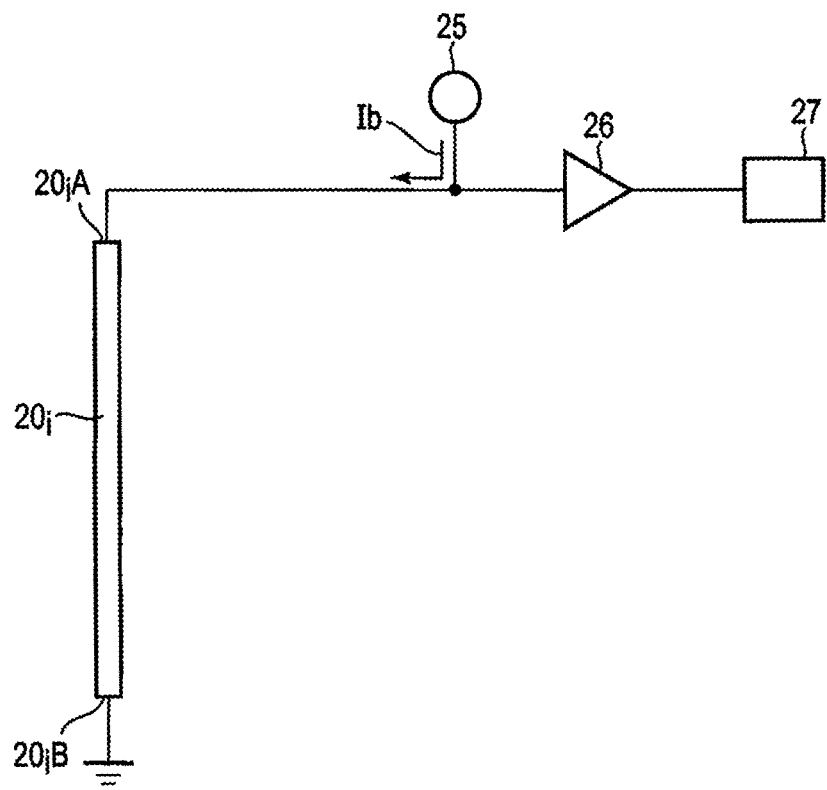
FIG. 3 is a diagram schematically showing a current source, an amplifier, and a measuring instrument connected to a superconducting strip of the particle detector.

As shown in FIG. 3, the particle detector may include a current source 25 connected to one end $20_iA$ of a superconducting strip $20_i$. The current source 25 supplies a bias current Ib to the superconducting strip $20_i$. The bias current Ib is smaller than the critical current of the superconducting material of the superconducting strip $20_i$. The other end $20_iB$ of the superconducting strip $20_i$ is connected to ground. When the current source 25 is not included in a part of the particle detector, the current source 25 is prepared when detecting an X-ray photon.

The particle detector may include an amplifier 26 connected to the one end $20_iA$ of the superconducting strip $20_i$. The amplifier 26 amplifies an electrical signal generated by the superconducting strip $20_i$. When the amplifier 26 is not included in a part of the particle detector, the amplifier 26 is prepared when detecting an X-ray photon.

The particle detector may include a measuring instrument 27 which is connected to the amplifier 26 and which is configured to monitor an electrical signal.

When an X-ray photon is absorbed by the superconducting strip $20_i$ in a superconducting state, which is cooled down to a critical temperature or less, a superconducting region of the superconducting strip $20_i$ is divided. Thus, detecting a state in which the superconducting region is divided (divided state) corresponds to detecting the X-ray photon. Here, when the divided state arises, the superconducting strip $20_i$ generates an electrical signal (for example, a pulsed electrical signal). Accordingly, the X-ray photon can be detected by detecting the electrical signal by using the measuring instrument 27.

When the measuring instrument 27 is not included in a part of the particle detector, the measuring instrument 27 is prepared when detecting an X-ray photon.

The superconducting strip $20_i$ is cooled down to the critical temperature or less by an optional refrigerator (not shown) so as to maintain the superconducting state. The refrigerator may not be included in the particle detector as in the case of the current source 25, the amplifier 26, etc.

Next, a method of detecting an X-ray photon using the particle detector of the present embodiment will be described.

As shown in FIG. 1, a sample 32 (for example, a semiconductor device) is disposed between the X-ray generator 31 and the fourth detection region $11_4$ (step S1). Next, the superconducting strip $20_i$ is cooled by the refrigerator to set the superconducting strip $20_i$ into a superconducting state (step S2). Next, the bias current Ib is supplied to the superconducting strip $20_i$ (step S3), and in this state, the sample 32 is irradiated with an X-ray generated by the X-ray generator 31, and an X-ray photon of the X-ray passes through the sample 32. The X-ray photon passed through the sample 32 is incident on the superconducting strip $20_i$. The bias current Ib is set to the extent that it is slightly less than the critical current, with which the superconducting state of the superconducting strip $20_i$ is maintained.

Figure 4:
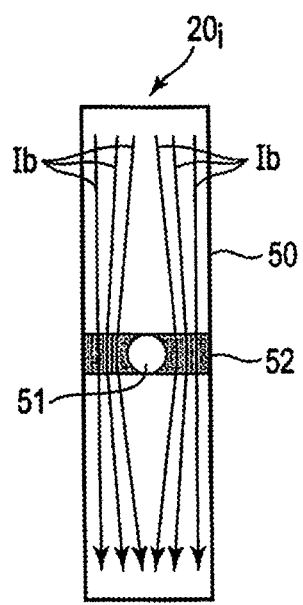
FIG. 4 is a diagram showing division of a superconducting region of the superconducting strip.

Since the width and the thickness of the superconducting strip $20_i$ are less than or equal to 200 nm, the sectional area of the superconducting strip $20_i$ is small. Thus, when an X-ray photon is absorbed in the superconducting strip $20_i$, a region called a hot spot (hereinafter, referred to as a hot spot region) 51, which transitions to a non-superconducting state, is generated in a superconducting region 50 of the superconducting strip $20_i$ as shown in FIG. 4. Since the electrical resistance of the hot spot region 51 increases, the bias current Ib bypasses the hot spot region 51 and flows through another region (bypass region) 52 as shown in FIG. 4. When a current greater than the critical current flows through the bypass region 52, the bypass region 52 transitions to a non-superconducting state and the superconducting region 50 is divided. Therefore, when the X-ray photon is incident on the superconducting strip $20_i$, a state (divided state) in which the superconducting region of the superconducting strip $20_i$ is divided arises (step S4).

Then, the hot spot region 51 and the bypass region 52, which have transitioned to a non-superconducting state, rapidly disappear by being cooled, and thus, a pulsed electrical signal is generated by temporary electrical resistance generated by the division of the superconducting region 50. The pulsed electrical signal is amplified by the amplifier 26, and the number of X-ray photons is detected by counting the amplified pulsed electrical signal by using the measuring instrument 27 (step S5).

Figure 5:
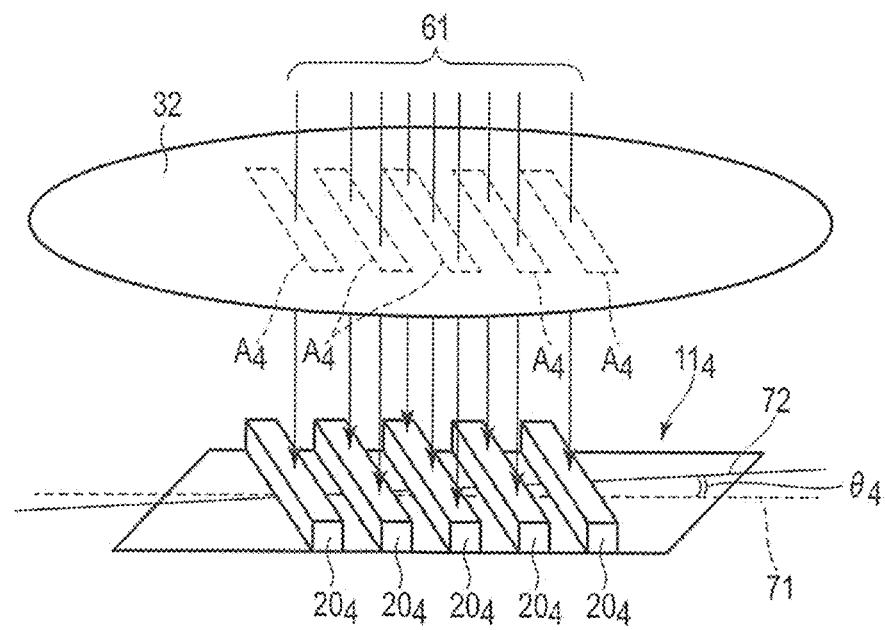
FIG. 5 is a diagram showing X-ray photons that pass through a sample and are incident on superconducting strips of the detection region.

Here, the number of detected X-ray photons, for example, as shown in FIG. 5, the number of X-ray photons detected by the fourth detection region $11_4$ corresponds to the number of X-ray photons 61 having passed through regions $A_4$ of the sample 32 corresponding to the superconducting strips $20_4$.

In FIG. 5, the number of X-ray photons 61 passed the region $A_4$ corresponding to the central fourth superconducting strip $20_4$ is three, each of the numbers of X-ray photons 61 passing the two regions $A_4$ corresponding to the two fourth superconducting strips $20_4$ adjacent to both sides of the central fourth superconducting strip $20_4$ is two, and each of the numbers of X-ray photons 61 passing the two regions $A_4$ corresponding to the outermost two fourth superconducting strips $20_4$ is one.

Note that, in FIG. 5, an angle $\theta_4$ represents an angle (inclination angle) formed by an optional axis (first axis) 71 selected as a standard and an axis (second axis) 72 parallel to the arrangement direction of the superconducting strips $20_4$. The angle (inclination angle) formed by the first axis 71 and the axis parallel to the arrangement direction of the superconducting strips $20_i$ will be hereinafter referred to as an angle $\theta_i$.

Figure 6A:
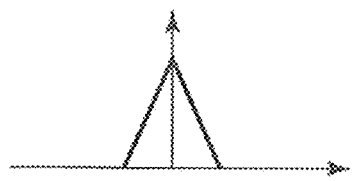
FIG. 6A, FIG. 6B, and FIG. 6C are diagrams showing an accumulated detection number profile of the X-ray photons that pass through the sample, a Fourier transform image profile of the accumulated detection number profile, and a Fourier transform image of an X-ray projection image of the sample.

A profile as shown in FIG. 6A is obtained by plotting positions in the arrangement direction of the fourth superconducting strips $20_4$ (direction parallel to the second axis 72) along the horizontal axis, and plotting the numbers of detected X-ray photons along the vertical axis. This profile is a profile of an accumulated detection number (accumulated detection number profile) which is obtained by accumulating the numbers of X-ray photons detected in the respective longitudinal directions of the fourth superconducting strips $20_4$ with respect to the positions in the arrangement direction of the fourth superconducting strips $20_4$.

In this manner, according to the present embodiment, the particle detector which can be used to generate an accumulated detection number profile of X-ray photons in the directions can be provided by adopting the structure in which the detection regions $11_i$ are stacked.

As an example showing the use of an obtained accumulated detection number profile, a difference between two different samples is evaluated. That is, the difference between the two different samples in a certain direction can be evaluated by comparing accumulated detection number profiles in the direction of the two different samples, and the difference between the two different samples can be evaluated in detail by similarly making a comparative evaluation in all the directions. At this time, if the directions (in the present embodiment, the directions D1 to D4) are equally distributed (in the present embodiment, the angle formed by the direction D1 and the direction D2, the angle formed by the direction D2 and the direction D3, and the angle formed by the direction D3 and the direction D4 are equal), the difference between the two different samples can be evenly evaluated. For example, if the samples have a geometrical pattern formed of horizontal and vertical sides, a minimum comparative evaluation can be made by selecting a total of four directions including two directions extending along the sides (horizontal direction and vertical direction) and two directions extending not along the sides (direction slanting upward to the left and direction slanting upward to the right) as the directions.

While the particle detector and the particle detection method for detecting X-ray photons have been described in the present embodiment, the present embodiment is also applicable to the detection of other particles. For example, the present embodiment is applicable to the detection of particles, such as extreme ultraviolet (EUV) photons, ultraviolet photons, infrared photons, visible light photons, electrons, neutrons, and ions.

Second Embodiment

Figure 7:
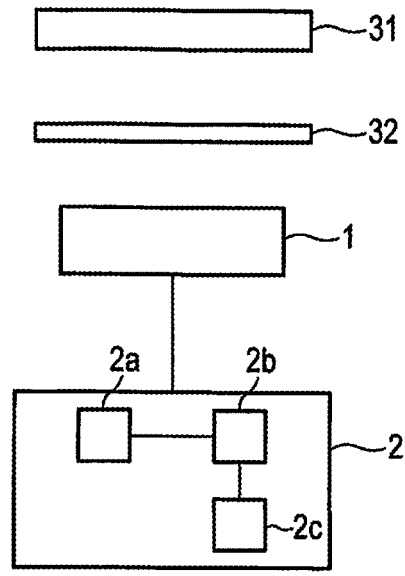
FIG. 7 is a block diagram showing a schematic structure of an image generation device according to a second embodiment.

FIG. 7 is a block diagram showing a schematic structure of an image generation device according to a second embodiment. In the image generation device of the present embodiment, the particle detector of the first embodiment is employed.

In FIG. 7, reference symbol 1 represents the particle detector of the first embodiment, and an image generator 2 is connected to the particle detector 1. More specifically, the image generator 2 is connected to the measuring instrument 27 shown in FIG. 3. The image generator 2 includes an accumulated detection number profile generator 2a, a Fourier transform image generator 2b, and an X-ray projection image generator 2c. Note that, in FIG. 7, the X-ray generator 31 is not included in the particle detector 1.

When the sample 32 is irradiated with X-rays, the particle detector 1 is irradiated with X-ray photons of the X-rays which pass through the sample (steps 10).

The accumulated detection number profile generator 2a generates accumulated detection number profiles, based on data measured by the measuring instrument 27 (step S11). The number of accumulated detection number profiles is equal to the number of stacked detection regions, and in the present embodiment, a first accumulated detection number profile to a fourth accumulated detection number profile are generated. More details are as follows.

The accumulated detection number profile generator 2a generates a profile of an accumulated detection number with respect to the positions in the arrangement direction of the superconducting strips $20_4$ (fourth accumulated detection number profile) which is obtained by accumulating data measured by the measuring instrument 27, that is, by accumulating the numbers of X-ray photons detected by the respective fourth superconducting strips $20_4$ along the longitudinal direction thereof.

The accumulated detection number profile generator 2a further generates a profile of an accumulated detection number with respect to the positions in the arrangement direction of the superconducting strips $20_3$ (third accumulated detection number profile) which is obtained by accumulating data measured by the measuring instrument 27, that is, by accumulating the numbers of X-ray photons detected by the respective third superconducting strips $20_3$ along the longitudinal direction thereof.

The accumulated detection number profile generator 2a further generates a profile of an accumulated detection number with respect to the positions in the arrangement direction of the superconducting strips $20_2$ (second accumulated detection number profile) which is obtained by accumulating data measured by the measuring instrument 27, that is, by accumulating the numbers of X-ray photons detected by the respective second superconducting strips $20_2$ along the longitudinal direction thereof.

The accumulated detection number profile generator 2a further generates a profile of an accumulated detection number with respect to the positions in the arrangement direction of the superconducting strips $20_2$ (first accumulated detection number profile) which is obtained by accumulating data measured by the measuring instrument 27, that is, by accumulating the numbers of X-ray photons detected by the respective first superconducting strips $20_1$ along the longitudinal direction thereof.

In the following description, if it is unnecessary to distinguish the first accumulated detection number profile to the fourth accumulated detection number profile in particular, they will be referred to as accumulated detection number profiles.

Figure 6B:
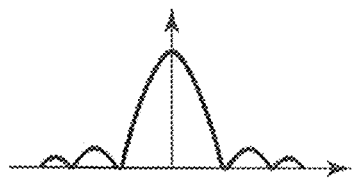
Figure 6C:
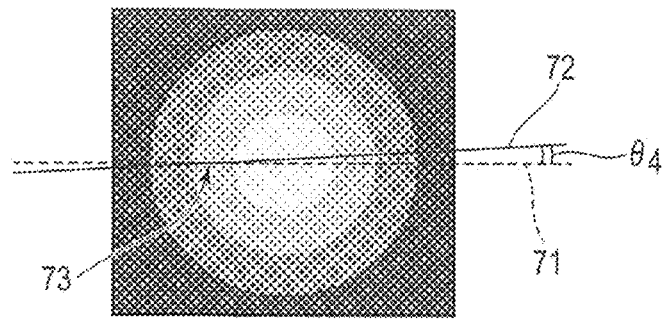

The first accumulated detection number profile to the fourth accumulated detection number profile are input to the Fourier transform image generator 2b. The Fourier transform image generator 2b performs Fourier transforms of the first accumulated detection number profile to the fourth accumulated detection number profile and generates a first Fourier transform image profile to a fourth Fourier transform image profile on the basis of the projection-slice theorem. FIG. 6B schematically shows a Fourier transform image profile obtained by performing a Fourier transform of an accumulated intensity profile of FIG. 6A. The Fourier transform image profile corresponds to a section (profile) in a direction defined by an angle $\theta_4$ of a Fourier transform image obtained by performing a Fourier transform of an X-ray projection image of a sample. The Fourier transform image generator 2b further generates a Fourier transform image of the X-ray projection image of the sample by drawing a contour line, based on the first Fourier transform image profile to the fourth Fourier transform image profile. FIG. 6C schematically shows the generated Fourier transform image.

The Fourier transform image of the X-ray projection image of the sample is input to the X-ray projection image generator 2c. The X-ray projection image generator 2c generates (reconstructs) an X-ray projection image of the sample by performing an inverse Fourier transform of the Fourier transform image of the X-ray projection image of the sample (step S12). This X-ray projection image is a projection image of X-rays that have passed through the sample.

Here, a medical computed tomography (CT) device performs X-ray radiation more than once, i.e., radiates an X-ray from an X-ray generator to a subject from different directions. However, in the present embodiment, the value of the angle $\theta_1$ is different for each of the detection regions, and thus the projection image can be obtained by performing X-ray radiation once. This leads to a reduction in the generation time of the X-ray projection image of the sample.

Figure 8:
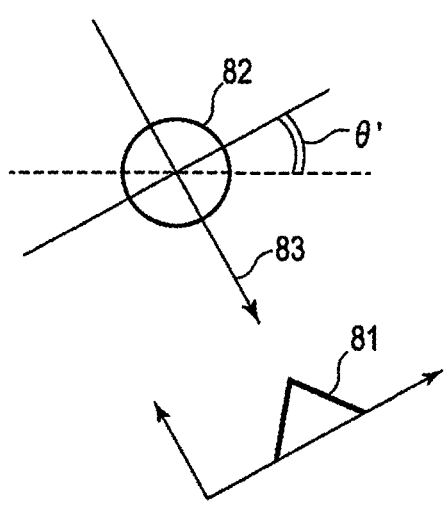
FIG. 8 is a diagram for explaining a projection-slice theorem.

In the projection-slice theorem, as shown in FIG. 8, the value of one point in an intensity profile 81 represents the number of X-ray photons (intensity) passing a sample with thickness (subject to be imaged) 82 in a direction 83, and an angle $\theta'$ is an angle of inclination defining the direction 83. That is, a direction in which an X-ray travels exists in a plane at the angle $\theta'$. A Fourier transform of the intensity profile 81 is performed, and a Fourier image is generated from contour lines of Fourier transform image profiles in all the angle $\theta'$, then an inverse Fourier transform of the obtained Fourier image is performed, and an image is thereby generated (reconstructed). Here, the generated (reconstructed) image is a two-dimensional sectional image (reconstructed image) of the sample 82 by the plane of the angle $\theta'$.

In contrast, in the present embodiment, data of one point in the intensity profile is a value obtained by accumulating the number of X-ray photons in the longitudinal directions of the superconducting strips $20_i$ in which the X-ray photons are those that pass through sample 32 and are incident on top surfaces of superconducting strips $20_i$ whose inclination angle is the angle $\theta_i$, and a traveling direction of the X-ray is perpendicular to the plane of the angle $\theta_i$. The generated (reconstructed) image (reconstructed image) is a projection image of the sample 32 projected on the plane of the angle $\theta_i$. By changing the relationship between the traveling direction of the X-ray and the angle $\theta'$ in the projection-slice theorem, not a two-dimensional sectional image but a projection image can be obtained by using a technique of the projection-slice theorem.

In order to obtain intensity data of a Fourier transform image as equally as possible, the angle $\theta_i$ is determined so that 0 to 180 degrees are equally divided by the number N of stacked layers.

In FIG. 6C, the intensity of the Fourier transform image profile in a region (crossing region) 73 where the intensity profiles of detection regions cross is proportional to a probability of detecting X-ray photons by the respective detection regions (detection rate) in which the X-ray photons are incident on the detection region of the highest layer. Since a probability that the X-ray photons reach the detection region decreases as the detection region disposed lower, the lower detection region has the smaller detection rate. In order to cancel a decrement of the intensity of the Fourier transform image profile due to the decline in the detection rate, for example, a correction is made by multiplying the intensity of the obtained Fourier transform image profile by a reciprocal number of the detection rate.

Figure 9A:
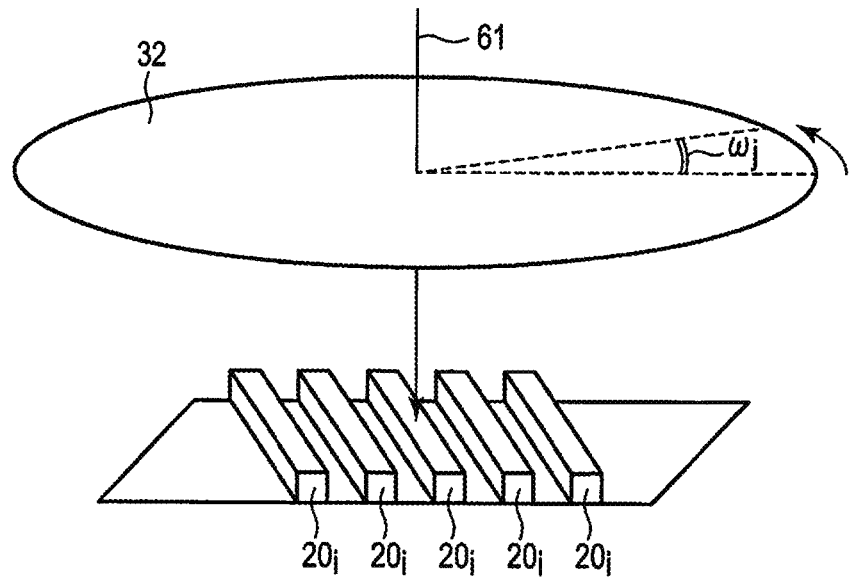
FIG. 9A and FIG. 9B are diagrams showing an X-ray photon which passes through a sample and is incident on superconducting strips of a detection region.

In addition, as shown in FIG. 9A, the sample 32 is rotated more than once at different angles $w_j$ of rotation (j=1, 2, . . . ) with respect to an axis (not shown) which is parallel to the traveling direction of an X-ray photon 61 and which passes through the center of the sample 32, and an accumulated detection number profile of each of the detection regions is obtained at the respective angles $\omega_j$ of the rotation, which corresponds to obtaining an accumulated detection number profile of each of the detection regions in a state in which the angle indicating the arrangement direction of the superconducting strips $20_i$ is changed from $\theta_i$ to $\theta_i$-$\omega_j$, and thus accumulated detection number profiles can be obtained in a larger number of arrangement directions of superconducting strips, or accumulated detection number profiles can be obtained in a less number of detection regions. At this time, the same positional relationship may be established by rotating the particle detector instead of rotating the sample 32.

Note that, FIG. 9A shows only one X-ray photon 61 for the sake of simplification. Further, the angle $\omega_j$ of rotation is given by, for example, $j \cdot \Delta\omega$. Here, j is a positive integer, and $\Delta\omega$ is a fixed value. Moreover, the angle $\omega_j$ of rotation may be irregularly changed instead of being changed by a positive integer multiple of $\Delta\omega$.

Figure 9B:
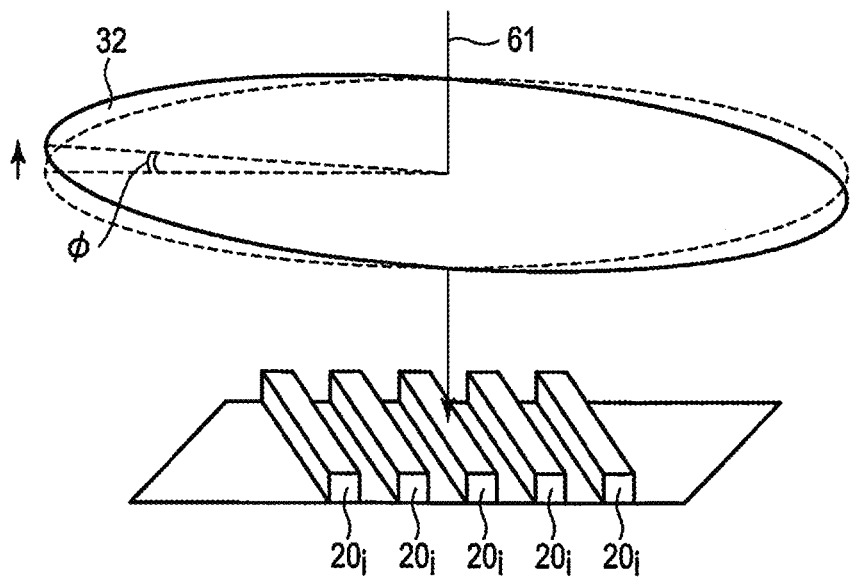

Furthermore, as shown in FIG. 9B, the angle $\Phi$ (angle of inclination) formed by a plane (surface) of the sample 32 to be irradiated with the X-ray photon 61 and a plane perpendicular to the axis parallel to the traveling direction of the X-ray photon 61 is changed by inclining the sample 32, and projection images are obtained at as many different angles $\Phi$ of inclination as possible. A three-dimensional image of the sample 32 can be obtained by performing reconstruction by using the technique of the projection-slice theorem, using all the obtained projection images at the angles $\Phi$ of the inclination. At this time, the same positional relationship may be established by inclining the traveling direction of an X-ray and the particle detector instead of inclining the sample 32. Noted that, FIG. 9B shows only one X-ray photon 61 for the sake of simplification.

Figure 10:
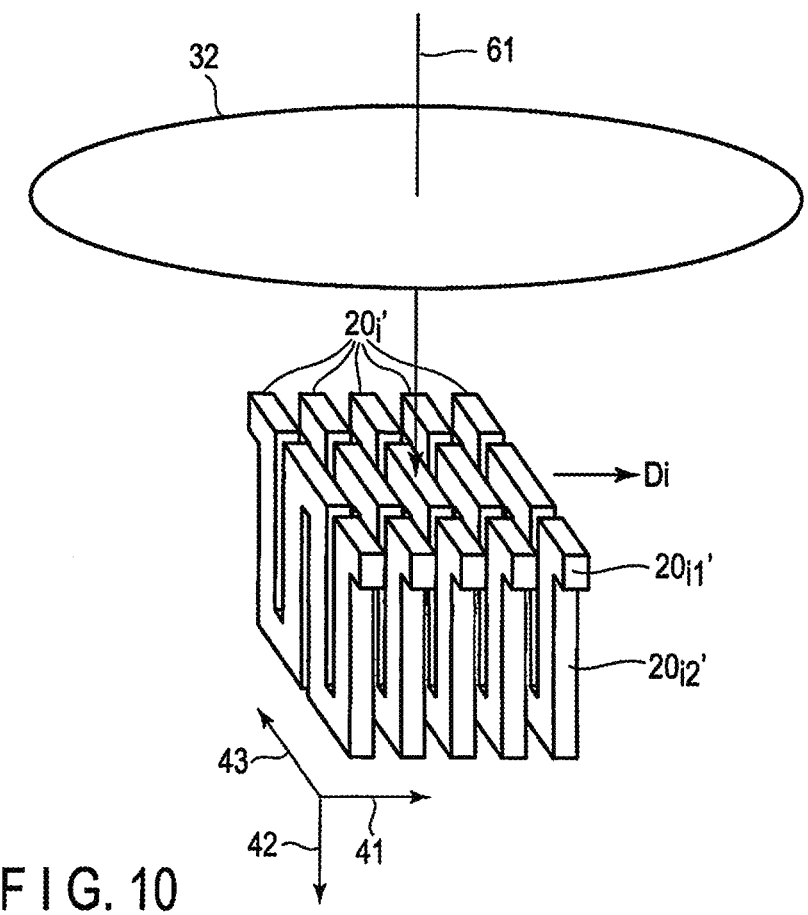
FIG. 10 is a perspective view showing the sample and meandering superconducting strips arranged below the sample.

It should be noted that meandering superconducting strips $20_{i'}$ shown in FIG. 10 may be used instead of the straight superconducting strips $20_i$ shown in FIG. 9A and FIG. 9B. In FIG. 10, reference symbol 41 represents an axis parallel to an arrangement direction Di of the superconducting strips $20_{i'}$, reference symbol 42 represents an axis parallel to the traveling direction of the X-ray photon 61, and reference symbol 43 represents an axis perpendicular to the axis 41 and the axis 42. The axis 41, the axis 42, and the axis 43 are orthogonal to each other.

The superconducting strip $20_{i'}$ has a structure in which a first straight portion $20_{i1'}$ extending along the axis 43 and a second straight portion $20_{i2'}$ extending along the axis 42 are alternately arranged.

A dimension along the axis 42 of the second straight portion $20_{i2'}$ is greater than a dimension along the axis 42 of the first straight portion $20_{i1'}$. Thus, the absorption probability of the X-ray photon 61 of the second straight portion $20_{i2'}$ is higher than the absorption probability of the X-ray photon 61 of the first straight portion $20_{i1'}$.

Figure 11:
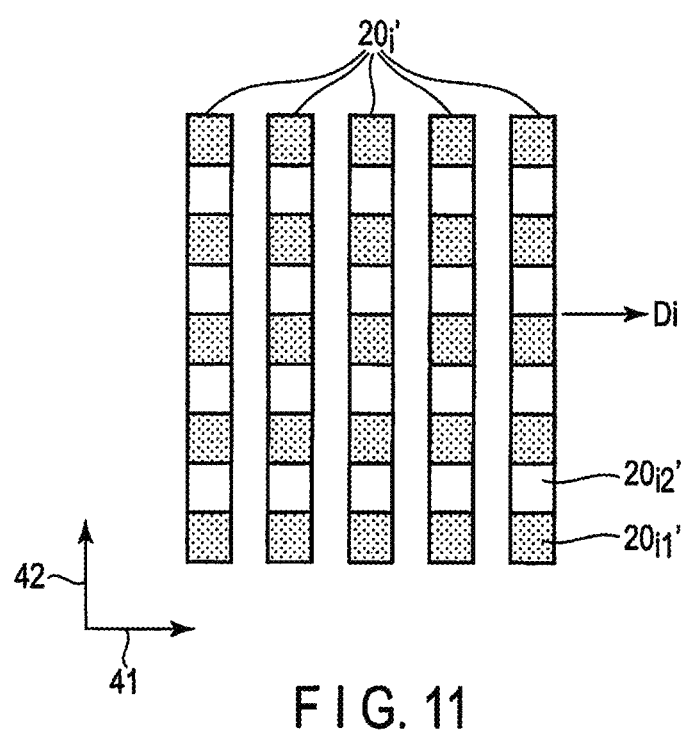
FIG. 11 is a plan view of the meandering superconducting strips.

As a result, as shown in FIG. 11, when the meandering superconducting strips $20_{i'}$ are viewed from the traveling direction of the X-ray photon 61, each of the meandering superconducting strips $20_{i'}$ has a structure in which the first straight portion $20_{i1'}$ having a lower absorption probability of the X-ray photon and the second straight portion $20_{i2'}$ having a higher absorption probability of the X-ray photon are periodically arranged. In FIG. 11, in order to easily distinguish the first straight portion $20_{i1'}$ and the second straight portion $20_{i2'}$, the first straight portion $20_{i1'}$ is represented by rectangles whose insides are gray, and the second straight portion $20_{i2'}$ is represented by rectangles whose insides are white.

An accumulated intensity profile obtained by the meandering superconducting strips $20_{i'}$ may be deformed from the accumulated intensity profile obtained by the straight superconducting strips $20_i$ shown in FIG. 9A and FIG. 9B. This deformation depends on the pattern on the sample 32 and can be predicted with the accumulated intensity profiles obtained with the other rotation angles $\omega_j$. Therefore, the accumulated intensity profile is calibrated so that the accumulated intensity profiles obtained with all of the angles $\omega_j$ could be consistent. An artifact is an image difference between the actual one and the reconstructed one, and is mainly caused by a noise on the accumulated intensity profile. This calibration executed with plural accumulated intensity profiles reduces the influence of the noise and also reduces the probability of occurrence of an artifact.

The meandering superconducting strips $20_{i'}$ include the second straight portion $20_{i2'}$ having the higher absorption probability of the X-ray photon, and thus the meandering superconducting strips $20_{i'}$ absorb more X-ray photons 61 than the straight superconducting strips $20_i$. Consequently, when the meandering superconducting strips $20_{i'}$ are used, the photons can be more efficiently counted.

Note that, the image generator 2 may constituted by using one generator, two generators, or four or more generators which have the function of accumulated detection number profile generator $2a$, the function of the Fourier transform image generator $2b$, and the function of the X-ray projection image generator $2c$. For example, when four or more generators is used, the function of the Fourier transform image generator $2b$ is implemented by different generators which includes a generator having the function of generating the first Fourier transform image profile to the fourth Fourier transform image profile, and another generator having the function of generating the Fourier transform image of the X-ray projection image of the sample.

In addition, if an evaluation portion (or an inspection portion) is added to the image generation device of the present embodiment, an inspection device (or an evaluation device) for evaluating (inspecting) the sample 32 also can be achieved. More specifically, an evaluation portion which evaluates the quality of the sample 32 (or an inspection portion which determines whether the sample 32 is defective or not), based on the projection image of the sample 32 generated by the image generator 2, is added. The evaluation portion (or the inspection portion) is connected to the image generator 2.

In addition, if an evaluation portion for evaluating a difference between two samples is used as the evaluation portion, the difference between the two samples can be evaluated on the basis of projection images of the two samples generated by the image generator 2.

Third Embodiment

When a sample 32 includes an array pattern 91 in which quadrangles 90 are periodically arranged as shown in FIG. 12A, a Fourier transform image 93 in which circles 92 are arranged in a lattice as shown in FIG. 12B is obtained by performing a Fourier transform of the array pattern 91.

In FIG. 12A, a period in a horizontal direction (X direction) of the array pattern 91 is represented by a, and a period in a vertical direction (Y direction) of the array pattern 91 is represented by b. The Y direction is perpendicular to the X direction.

A spatial frequency corresponding to the period a of FIG. 12A is 1/a, and a spatial frequency corresponding to the period b of FIG. 12A is 1/b. In FIG. 12B, lattice points appear at intervals of 1/a in the horizontal direction and at intervals of 1/b in the vertical direction, and lattice points appear at the positions of (m/a, n/b), where n and m are optional integers. In other words, the lattice points of the Fourier transform image appear on a line 94 whose inclination is defined by $\tan^{-1}\{(n \cdot a/m \cdot b)\}$.

Thus, when the sample 32 includes the array pattern 91 (periodic pattern), the number of stacked detection regions can be reduced by adopting an angle defined by $\tan^{-1}\{(n \cdot a/m \cdot b)\}$ as the angle $\theta_4$ of inclination of FIG. 6A since the lattice points included in the Fourier transform image of the X-ray projection image is increased. In addition, the closer the integers n and m are to 0, the more the lattice points included in the Fourier transform image of the X-ray projection image increase.

For example, in a case in which n and m are each any one of −1, 0 and 1, the angle θ is 0 degrees when n is 0 and m is −1 or 1, the angle θ is $\tan^{-1}(a/b)$ degrees when n is 1 and m is 1, or n is −1 and m is −1, the angle θ is 90 degrees when n is −1 or 1 and m is 0, and the angle θ is $180-\tan^{-1}(a/b)$ degrees when n is −1 and m is 1, or n is 1 and m is −1.

Fourth Embodiment

Figure 13:
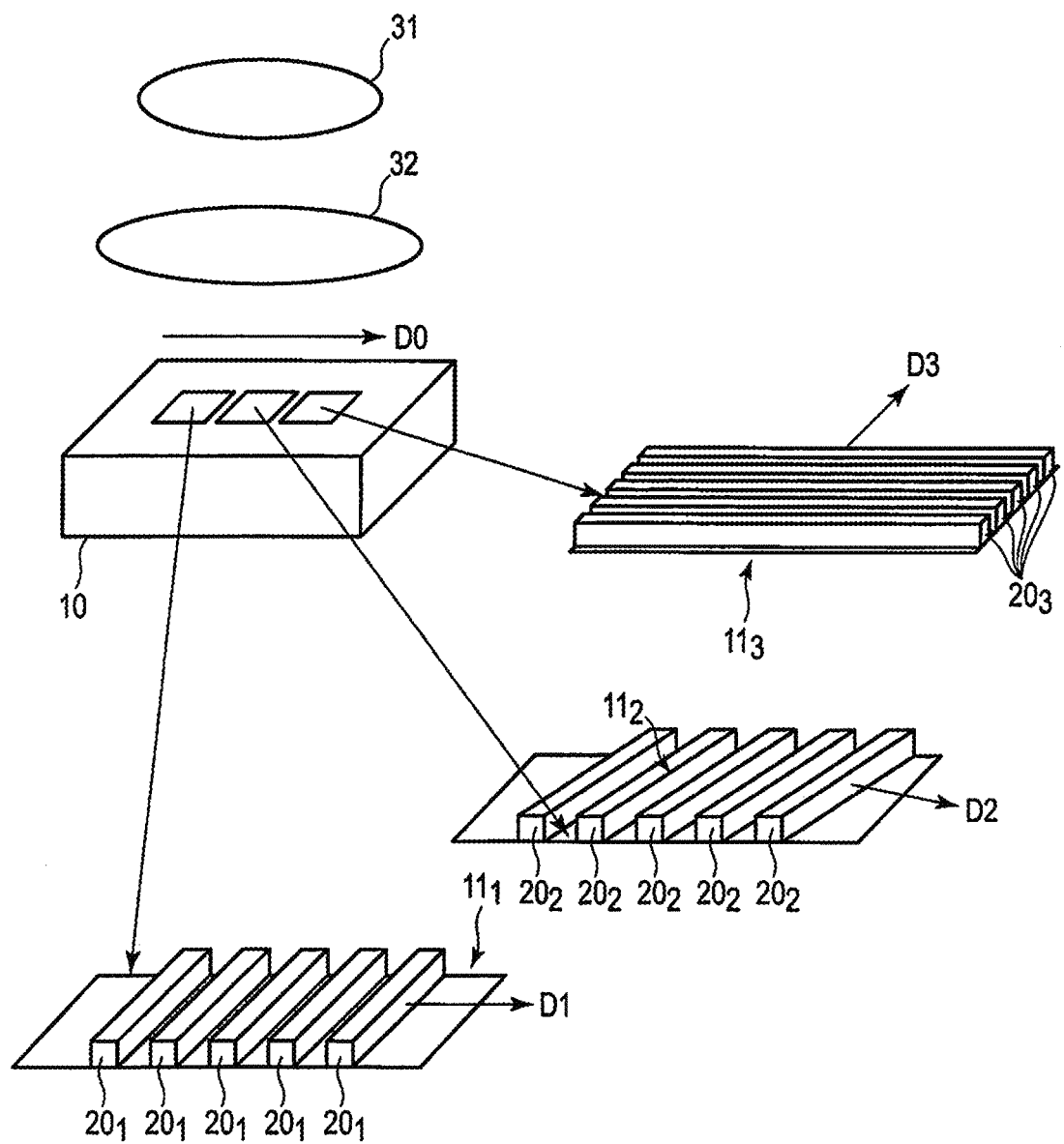
FIG. 13 is a perspective view showing a schematic structure of a particle detector according to a fourth embodiment.

FIG. 13 is a perspective view showing a schematic structure of a particle detector according to a fourth embodiment.

In the first embodiment, detection regions are stacked, whereas in the present embodiment, detection regions $11_i$ are arranged to be in contact with a surface (common surface) of a substrate 10 as shown in FIG. 13. The detection regions $11_i$ are arranged along a direction D0. Noted that, in FIG. 13, the number of detection regions is three for the sake of simplification. In addition, although a slit portion is not shown in FIG. 13, the slit portion may be used as in the case of the first embodiment.

FIG. 14A to FIG. 14C are diagrams for explaining a particle detection method employing the particle detector of the present embodiment.

First, as shown in FIG. 14A, a sample 32 is irradiated with an X-ray (not shown), and the number of X-ray photons 61 of the X-ray that have passed through a predetermined region 33 of the sample 32 is detected by a first detection region $11_1$.

Next, as shown in FIG. 14B, the sample 32 is scanned in the direction D0, and the number of X-ray photons 61 that have passed through the predetermined region of the sample 32 is detected by a second detection region $11_2$.

In addition, as shown in FIG. 14C, the sample 32 is scanned in the direction D0, and the number of X-ray photons 61 that have passed through the predetermined region of the sample 32 is detected by a third detection region $11_3$.

FIG. 15A to FIG. 15D are diagrams for explaining another particle detection method employing the particle detector of the present embodiment. According to this particle detection method, the numbers of X-ray photons 61 that have passed through predetermined regions 33a and 33b of the sample 32 are detected. FIG. 15A to FIG. 15D show the two regions 33a and 33b successively arranged in the direction D0.

First, as shown in FIG. 15A, the sample 32 is irradiated with X-rays (not shown), and the number of X-ray photons 61 of the X-rays that passed through the predetermined region 33a of the sample 32 is detected by the first detection region $11_1$.

Next, as shown in FIG. 15B, the sample 32 is scanned in the direction D0, and the number of X-ray photons 61 that have passed through the predetermined region 33a of the sample 32 and the number of X-ray photons 61 have passed through the predetermined region 33b of the sample 32 are detected in the second detection region $11_2$ and the first detection region $11_1$, respectively.

Next, as shown in FIG. 15C, the sample 32 is scanned in the direction D0, and the number of X-ray photons 61 have passed through the predetermined region 33a of the sample 32 and the number of X-ray photons 61 have passed through the predetermined region 33b of the sample 32 are detected in the third detection region $11_3$ and the second detection region $11_2$, respectively.

In addition, as shown in FIG. 15D, the sample 32 is scanned in the direction D0, and the number of X-ray photons 61 have passed through the predetermined region 33b of the sample 32 is detected by the third detection region $11_3$.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A particle detector comprising:
   a substrate; and
   detection regions provided on the substrate and insulated from the substrate, each of the detection regions comprising superconducting strips having a longitudinal direction and configured for detecting a particle on a certain particle arrival region, the superconducting strips being arranged in arrangement directions differing between the detection regions, wherein:
the number of the detection regions is three or more,
the number of particles detected by the respective detection regions are used to generate accumulated detection number profiles of particles in the arrangement directions of the superconducting strips of the respective detection regions,
each of the accumulated detection number profiles includes a profile obtained by accumulating the numbers of particles detected by the respective superconducting strips along the longitudinal direction, and
the accumulated detection number profiles of the particles are used to reconstruct a two-dimensional distribution of the number of particles on the certain particle arrival region.

2. The particle detector of claim 1, wherein the two-dimensional distribution of the number of particles on the certain particle arrival region is reconstructed by using a technique of projection-slice theorem.

3. The particle detector of claim 1, wherein the respective arrangement directions of the superconducting strips are equally distributed.

4. The particle detector of claim 1, wherein the detection regions are stacked in an insulated state, or arranged in a same plane in an insulated state.

5. The particle detector of claim 1, wherein:
the detection regions include a first detection region, a second detection region, a third detection region, and a fourth detection region,
the first detection region includes first superconducting strips and the arrangement direction thereof is a first direction,
the second detection region includes second superconducting strips and the arrangement direction thereof is a second direction different from the first direction,
the third detection region includes third superconducting strips and the arrangement direction thereof is a third direction different from the first direction and the second direction,
the fourth detection region includes fourth superconducting strips and the arrangement direction thereof is a fourth direction different from the first direction, the second direction, and the third direction,
the number of particles detected by each of the first superconducting strips is used to generate a first accumulated detection number profile,
the number of particles detected by each of the second superconducting strips is used to generate a second accumulated detection number profile,
the number of particles detected by each of the third superconducting strips is used to generate a third accumulated detection number profile, and
the number of particles detected by each of the fourth superconducting strips is used to generate a fourth accumulated detection number profile.

6. The particle detector of claim 1, wherein each of the superconducting strips has a linear shape.

7. The particle detector of claim 1, wherein each of the superconducting strips has a meandering shape.

8. The particle detector of claim 1, wherein the particles are those that have passed through a sample.

9. An image generation device comprising:
the particle detector of claim 1; and
a generator which generates the accumulated detection number profiles based on the number of particles detected by the respective detection regions of the particle detector, and reconstructs a two-dimensional distribution of the number of particles on the certain particle arrival region by using the accumulated detection number profiles.

10. The image generation device of claim 9, wherein the respective arrangement directions of the superconducting strips are equally distributed.

11. The image generation device of claim 9, wherein the detection regions are stacked in an insulated state, or arranged in a same plane in an insulated state.

12. The image generation device of claim 9, wherein the generator reconstructs the two-dimensional distribution of the number of particles on the certain particle arrival region by using the accumulated detection number profiles of the particles with a technique of projection-slice theorem.

13. An image generation method employing the particle detector of claim 1,
the image generation method comprising:
irradiating the particle detector with particles that passed through a sample by irradiating the sample with particles;
generating the accumulated detection number profiles based on the number of particles detected by the respective detection regions of the particle detector; and
reconstructing a two-dimensional distribution of the number of particles on the certain particle arrival region by using the accumulated detection number profiles.

14. The image generation method of claim 13, wherein the number of particles detected by the respective detection regions of the particle detector are those that are detected by the respective detection regions at different angles of rotation by rotating any one of the sample and the particle detector more than once at the different angles of rotation with respect to an axis parallel to the traveling direction of the particles.

15. The image generation method of claim 13, wherein reconstructing the two-dimensional distribution of the number of particles on the certain particle arrival region by using the accumulated detection number profiles is performed with a technique of projection-slice theorem.

16. The image generation method of claim 15, wherein the reconstructed two-dimensional distribution of the number of particles on the certain particle arrival region is a projection image of the sample through which the particles passed.

17. The image generation method of claim 16, wherein the reconstructed image includes a three-dimensional image, and
generating the three-dimensional image comprising obtaining projection images of the sample by varying an angle formed by a plane of the sample to be irradiated with the particles and a plane perpendicular to the axis.

18. A particle detector comprising:
a substrate; and
detection regions provided on the substrate and insulated from the substrate,
each of the detection regions comprising superconducting strips having a longitudinal direction and configured for detecting a particle on a certain particle arrival region, the superconducting strips being arranged in arrangement directions differing between the detection regions, wherein:

the number of the detection regions is three or more, each of the detection regions includes the certain particle arrival region, the number of particles detected by the respective detection regions are used to generate accumulated detection number profiles of particles in the arrangement directions of the superconducting strips of the respective detection regions, each of the accumulated detection number profiles includes a profile obtained by accumulating the number of particles detected by the respective superconducting strips along the longitudinal direction, and the accumulated detection number profiles of the particles on the certain particle arrival region are used to compare with other accumulated detection number profiles of the particles on other certain particle arrival region to evaluate the similarity between the particles on the certain particle arrival region and the particles on the other certain particle arrival region.

19. The particle detector of claim 1, wherein:

the detection regions include a first detection region, a second detection region and a third detection region, the first detection region includes first superconducting strips and the arrangement direction thereof is a first direction, the second detection region includes second superconducting strips and the arrangement direction thereof is a second direction different from the first direction, the third detection region includes third superconducting strips and the arrangement direction thereof is a third direction different from the first direction and the second direction, the number of particles detected by each of the first superconducting strips is used to generate a first accumulated detection number profile, the number of particles detected by each of the second superconducting strips is used to generate a second accumulated detection number profile, and the number of particles detected by each of the third superconducting strips is used to generate a third accumulated detection number profile.

\* \* \* \* \*